United States Patent [19]

Stalling et al.

[11] Patent Number: 5,198,115
[45] Date of Patent: Mar. 30, 1993

[54] INTEGRATED INSTRUMENT FOR SUPERCRITICAL FLUID SAMPLE EXTRACTION, SAMPLE SEPARATION AND CONCENTRATION

[75] Inventors: David L. Stalling; Said Saim, both of Columbia, Mo.

[73] Assignee: Analytical Bio-Chemistry Laboratories, Inc., Columbia, Mo.

[21] Appl. No.: 727,464

[22] Filed: Jul. 9, 1991

[51] Int. Cl.$^5$ .......................................... B01D 11/04
[52] U.S. Cl. .................................. 210/634; 210/137
[58] Field of Search .............. 210/634, 637, 97, 137, 210/130, 642, 644, 649

[56] References Cited

PUBLICATIONS

Analuytical-Scale Supercritical Fluid Extraction, pp. 633A to 642A by Steven B. Hawthorne Analytical Chemistry vol. 62 No. 11, Jun. 1, 1990.
Extraction of Pesticides from Soil with Supercritical $CO_2$ by H. Engelhardt, Journal of High Resolution Chromatography & Chromatography Communications, p. 726, 1988.
Fundamentals and Applications of Supercritical Fluid Extraction in Chromatographic Science, by Jerry W. King pp. 355-364, Journal of Chromatographic Science, vol. 27 Jul. 1969.
Exclusion Chromatography in Dense Gases: An Approach to Viscosity Optimization by J. Calvin Giddings et al, pp. 243-249 Analytical Chemistry, vol. 49, No. 2, Feb. 1977.
Size Exclusion Chromatography of Polystyrenes with Supercritical Dichloromethane by Chuzo Fujimoto et al Journal of Chromatographic Science, vol. 27, Jun. 1969 pp. 325 and 327.
Supercritical Fluid Extraction Enhancer, PB90-238114 (U.S. Agricultural Research Service, Jun. 12, 1990.
On-Line Supercritical Fluid Extraction/Chromatography System for Trace Analysis of Pesticides in Soybean Oil and Rendered Fats by B. Murugaverl et al J. Microcol. Sep. 3 11-16 (1991).

Primary Examiner—Frank Sever

[57] ABSTRACT

An integrated sample extraction and separation system includes a number of substantially identical supercritical fluid extraction modules and sample separation modules connected in common to a source of supercritical fluid and modifier and to instruments for sample analysis. Each of the supercritical fluid extraction columns is provided with separate pressure and temperature controls. Preferably, each sample separation module provides the choice of sample separation by dissolving the extracted sample in solvent, by adsorption, or by size exclusion chromatography. Either the supercritical fluid or various solvents may be used as the mobile phase in the sample separation step.

50 Claims, 2 Drawing Sheets

FIG 1

DRAIN OR SAMPLE COLLECTION

FIG 2

INTEGRATED INSTRUMENT FOR SUPERCRITICAL FLUID SAMPLE EXTRACTION, SAMPLE SEPARATION AND CONCENTRATION

BACKGROUND OF THE INVENTION

1. Field of the Invention

This invention relates to improved instruments for supercritical fluid extraction of environmental, biological and other samples of materials from matrices, and for subsequent separation, clean up and concentration of the extracted samples, for example, to enrich the analytes for efficient chromatographic separation and identification. More particularly, this invention relates to an integrated instrument for performing supercritical fluid sample extraction and then separating the sample into its constituent parts, providing substantially unlimited control of the pertinent process parameters, while permitting a relatively large number of sample extraction and separation processes to be operated simultaneously and in parallel.

2. Description of the Prior Art

The science of identifying and quantifying the constituents of a sample, having been separated from one another, has advanced very substantially in the last few years. However, the process of separating typical contaminants, such as pesticides, from the matrices in which they are found, such as food products, soils and the like, has until quite recently remained relatively primitive. As stated by Hawthorne, "Analytical-Scale Supercritical Fluid Extraction", Analytical Chemistry, 62, No. 11 (1990), the sample extraction procedures employed by most laboratories have not changed since the initial reporting of chromatography in 1906, and many laboratories continue to rely on multiple distillation processes employing the so-called Soxhlet apparatus to remove the sample from the matrix.

Recently, as discussed in detail by Hawthorne, supercritical fluid extraction has been employed by more and more laboratories. A supercritical fluid is one which is above its critical temperature and pressure, such that it cannot be liquefied regardless of any increase in pressure. In this region of the state diagram of the material, it exhibits gas-like mass transfer and liquid-like solvating characteristics. That is, a supercritical fluid readily penetrates a matrix as might a gas, while materials in the matrix are dissolved by the supercritical fluid and extracted as if it were a liquid. Sample extraction using supercritical fluids is normally much faster and much simpler than repeated distillation in a Soxhlet apparatus. As supercritical fluid extraction need not be carried out at the very high temperatures characteristic of repeated distillation separation processes, thermally unstable compounds can be extracted without damage. Supercritical fluid extraction is commonly carried out using $CO_2$ as the supercritical fluid, thus avoiding use of numerous solvents now identified as potential carcinogens such as methylene chloride, and eliminating a substantial safety hazard. Accordingly, supercritical fluid extraction of samples from matrices has become increasingly popular in recent years.

In addition to the Hawthorne article already mentioned, numerous references discuss supercritical fluid extraction. See, for example, King, "Fundamentals and Applications of Supercritical Fluid Extraction and Chromatographic Science", J. Chromatographic Sci., Vol. 27, p. 335-364 (1989); Englehardt et al, "Extraction of Pesticides from Soil with Supercritical $CO_2$", J. High Resolution Chromatography and Chromatography Communications, 10772, p. 726 (1988); Katauskas et al, "SFE: Will It Solve Your Lab's Solvent Waste Problems?" R & D, March 1991, p. 39, 41-44; Parkinson et al, "Supercritical Processes Win CPI Acceptance", Chem. Eng., (July 1989), p. 35, 37, 39; Bosta et al, "Supercritical Fluids: Still Seeking Acceptance", Chem. Eng., (Feb. 4, 1985).

Other prior art references of relevance to this work suggest the use of supercritical fluids as the mobile phase in various types of chromatography. For example, Giddings et al, "Exclusion Chromatography in Dense Gases: An Approach To Viscosity Optimization", Anal. Chem., 49, No. 2 (1977) discusses the use of supercritical fluids for size exclusion chromatography of polymers in a porous silica column. Fujimoto et al, "Size Exclusion Chromatography of Polystyrenes with Supercritical Dichloromethane", J. Chromatographic Science, 27, 325, 327 (1989) discusses supercritical fluid separation of polymers by size exclusion chromatography using a porous glass matrix. However, many of the resins and other materials used for size exclusion chromatography, e.g. S-X3 resin, are not suitable for use with supercritical fluids as they degrade at the high pressures and/or relatively high temperatures required.

Other references suggest the use of particular materials such as the diatomaceous earth sold by Analytichem International as "ChemTube-Hydromatrix" for removal of moisture in supercritical fluid extraction; see Hopper et al U.S. patent application Ser. No. 07/536,861 filed Jun. 12, 1990.

Various operational parameters useful in supercritical fluid extraction are summarized by Hawthorne, supra, including the use of organic modifier solvents in addition to the supercritical fluid for extraction of relatively polar sample materials from matrices. Hawthorne also notes that the solvent strength of the supercritical fluid varies with its temperature and pressure and that these parameters can be usefully controlled for selective extraction of various samples from matrices.

The prior art also suggests combination of supercritical fluid extraction (SFE) with solid phase extraction and supercritical fluid chromatography (SFC) for on line extraction, separation, and analysis of lipid-loaded, low analyte content biological samples. See Murugaverl et al, "On-line Supercritical Extraction/Chromatography System for Trace Analysis of Pesticides in Soybean Oil and Rendered Fats", J. Microcol. Sep., 3, p. 11-16 (1991). The apparatus discussed in this reference employs a supercritical fluid extraction cell followed by a column packed with adsorbent silica or the like, and then by a fused silica capillary column for supercritical fluid chromatography (SFC). Lipid extracts are selectively retained in the packed column, and the pesticides are then concentrated by cryofocussing prior to SFC analysis. Their apparatus does not lend itself to automatic operation, as the adsorbent silica material retains high polarity substances such as organophosphate pesticides. King in the J. Chromatographic Science article supra also discusses the advantages of combining supercritical fluid extraction with selective adsorption of lipids on silica or alumina packing. Various adsorbents useful for supercritical fluid separation are summarized by Hawthorne, supra.

The art shows various commercially available instruments for supercritical fluid extraction of relatively small size (0-20 g) samples from solid or semi-solid matrices, in some cases combined with subsequent sample separation units. For example, Fisons Instruments, Valencia, Calif., offers a "Supercritical Fluid Extractor", Model SFE 30, that allows programming of the pressure of the supercritical fluid to effect selective extraction, and provides means for addition of small amounts of organic modifier to allow extraction of relatively polar analytes. The proportion of supercritical fluid to modifier can be varied through the use of two pumps.

Isco, Inc., Lincoln, Nebr., offers a Model SFX 2-10 Supercritical Fluid Extractor. This device accepts dual extraction columns but does not allow simultaneous extraction of both samples. A sample may be loaded in one column while the contents of the second column are being extracted. The Isco system provides temperature control from ambient up to 150° C. Variable flow rates of supercritical fluids and modifiers are delivered by two separate refillable syringe pumps. Their outputs can be joined at a tee fitting to provide a mixture of supercritical fluid and modifier in any desired ratio.

Suprex Corporation, Pittsburgh, Pa., manufactures high pressure SFE and SFC instruments. This company offers a versatile Model MPS/225 instrument that can perform on-line SFE-SFC, SFE only, SFC only, on-line and off-line SFE followed by gas chromatography, or on-line SFE and off-line SFE followed by liquid chromatography. The Suprex device also provides for addition of solvent modifiers to the supercritical fluid.

Computer Chemical Systems, Inc., Avondale, Pa., offers a line of instruments for supercritical fluid extraction and chromatography. The Model 3200 multi-sample SFE system of this company provides for either simultaneous or sequential extraction of up to six samples. An air-driven pump is used to provide sufficient flow through all six columns. Both SFE and SFC units are microprocessor controlled, including injection valve operation, temperature and pressure. The SFC 5000 system is stated to allow unattended operation of up to sixty total sample runs using twenty sample vials. On-line mixing of supercritical fluid and an organic modifier such as methanol is also possible.

Hewlett Packard offers the HP7680A Supercritical Fluid Extractor featuring a variable restrictor nozzle allowing supercritical flow rates to be set independent of density and temperature. The system is apparently intended to be used with a variety of adsorption trap packings and can accept up to twenty-one collection vials for sample collection. This system is computer controlled using a Microsoft Windows-based system.

Newport Scientific, Jessup, Md., offers a pilot size supercritical fluid extraction system that features a large capacity diaphragm compressor capable of delivering either gas or liquid, and both large capacity SFE column and large capacity sample collection vessels. The flow direction through the extractor may be reversed by means of manually operated valves.

It can thus been seen that while the prior art has made use of supercritical fluid sample extraction combined with a wide variety of chromatographic sample separation techniques, the prior art does not show a fully automated integrated instrument providing SFE followed by supercritical fluid sample separation, including a large number of separate supercritical fluid extraction modules with independent temperature, pressure and flow rate control. Such an instrument is of great importance for laboratories processing large numbers of large and small samples, and for development of analytical methods, requiring flexibility in extraction and separation parameters.

OBJECTS AND SUMMARY OF THE INVENTION

It is therefore an object of the invention to provide an improved integrated supercritical fl id extraction instrument including a plurality of substantially identical supercritical fluid extraction modules, all connected to the same source of supercritical fluid and organic modifier.

It is a further object of the invention to provide an integrated instrument and a corresponding method for sample extraction and subsequent separation, the instrument comprising a plurality of identical supercritical fluid extraction modules, each associated with a corresponding sample separation device, at least some of which include size exclusion chromatographic columns and associated equipment, whereby supercritical fluid extraction and size exclusion chromatography can be employed to extract a sample from a matrix and subsequently separate the sample into its constituent parts, and wherein either the supercritical fluid or a solvent may be employed as the mobile phase for size exclusion chromatography.

It is a further object of the invention to provide an instrument offering unparalleled flexibility in selection of operational parameters for both supercritical fluid extraction of a sample from a matrix and for subsequent sample separation.

It is a further object of the invention to provide an instrument employing a number of essentially similar supercritical fluid extraction and subsequent sample separation modules, wherein the supply of supercritical fluid and modifier is common to each module, and the analysis performed on the separated samples is carried out employing common analytical apparatus, providing substantial economies in the overall system cost.

It is a further object of the invention to provide an integrated supercritical fluid extraction system comprising a number of identical supercritical fluid extraction modules each coupled with plural sample separation devices, wherein the sample separation process to be employed in connection with each of the sample extraction modules can be separately selected, and such that the pressure and temperature conditions prevailing in each of the sample extraction columns and sample separation units can be separately controlled for further system flexibility.

It is a further object of the invention to provide an integrated instrument for performing on-line separation and concentration of SFE sample extracts obtained from any SFE instrument, and wherein sample concentration and separation can be performed using either a conventional or a supercritical fluid as the mobile phase.

The above needs of the art and objects of the invention are met by the present invention of an integrated sample extraction and separation instrument. The instrument includes a number of substantially identical supercritical extraction modules, each comprising a supercritical fluid extraction column, means for controlling the pressure in and the pressure drop across the column, and means for controlling the temperature thereof. The supercritical fluid extraction modules are connected to a manifold coupled to a source of supercritical fluid and modifier. The relative proportions of supercritical fluid and modifier may be conveniently varied. Each of the supercritical extraction modules is connected to a sample separation module. At least some of the sample separation modules include size exclusion chromatography columns, and each preferably includes apparatus permitting the choice between plural separation processes. Plural series-connected or bypassable size-exclusion chromatography columns may be provided. More preferably, each sample separation module comprises selectible apparatus for at least one of size exclusion chromatography, adsorptive separation, and solvation of a sample in a quantity of solvent; two of these processes may be employed in sequence as well. The system allows selection between one or more liquid solvents or the supercritical fluid provided by the SFE unit as the mobile phase for both adsorptive and size exclusion separation.

BRIEF DESCRIPTION OF THE DRAWINGS

The invention will be better understood if reference is made to the accompanying drawings wherein like reference numerals in the various figures represent like components, and wherein.

DESCRIPTION OF THE PREFERRED EMBODIMENTS

It will be recognized by those of skill in the art of analysis of, for example, environmental samples that the terms "separation" and "clean-up" overlap to some extent; in general "clean-up" is used to refer to separation of classes of chemicals from one another, such as lipids from pesticides, while "separation" refers to fractionation of a group of related molecules, e.g. a mixture of polymers, from one another. The term "separation" as used herein is to be understood to include "clean-up" unless the context dictates otherwise.

Figure 1:
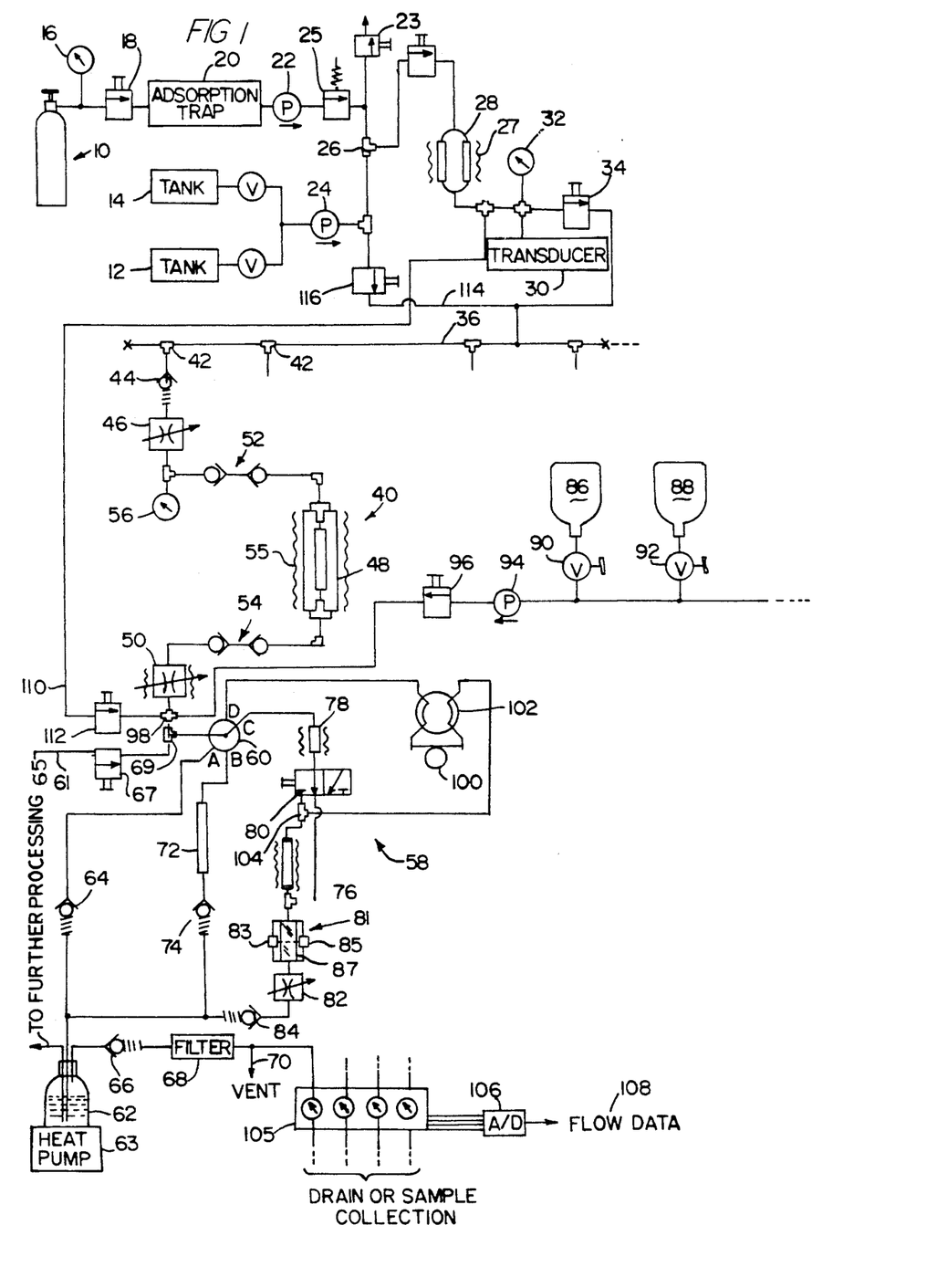
FIG. 1 is an overall schematic flow diagram of the system of the invention, including one of a plurality of identical supercritical fluid extraction modules and sample separation modules.

The integrated supercritical fluid sample extraction and separation instrument according to the invention, in one preferred embodiment shown in FIG. 1, comprises a supercritical fluid supply section, supplying either pure supercritical fluid or a binary mixture of the pure supercritical fluid with an organic modifier solvent, a number of essentially identical supercritical fluid extraction modules, and a like number of corresponding sample separation modules which may also all be identical.

Referring now to FIG. 1, the supercritical fluid and modifier supply section comprises a tank 10 containing either a liquid or a liquified gas. This material may be $CO_2$, $N_2O$, or any other material useful as a supercritical fluid for separation of a sample from a matrix. The supply section further comprises one or more tanks 12, 14 of different organic modifiers known to the art, such as toluene or methanol, together with associated valving and piping. The pressure of the fluid in tank 10 is monitored by a pressure gauge 16 and its flow is controlled by a valve 18. The fluid is passed through an adsorption trap 20 filled with activated carbon, alumina or the like to remove moisture or trace contaminants. Fluid flow rate and pressure are controlled as needed by controllable pump 22, which may be either a generally conventional pump or a more specialized pump. The modifier pressure is increased by a second similar pump 24. The fluids are mixed at a tee fitting 26. Their relative proportions are controlled by the relative pumping rates of pumps 22 and 24. A regulating relief valve 25 and a vent valve 23 are provided to regulate $CO_2$ (or other fluid) flow through the lines, and to prime the pumps 22 and 24 respectively.

The mixture of modifier and supercritical fluid is stored in a receiver 28 in order to damp out pressure pulsations in the line and to provide a stable source of supply of the supercritical mixture. Receiver 28 is heated by a heater indicated schematically at 27, such that the mixture in the receiver is maintained at desired supercritical conditions.

The pressure of the fluid in receiver 28 is monitored by a transducer 30 and a gauge 32. Fluid flow is activated by opening shut-off valve 34. The mixture is supplied to a manifold 36 connected to a number of essentially identical supercritical fluid extraction modules 40, only one such module being shown in FIG. 1 to avoid repetition and preserve clarity. Each extraction module 40 is connected to the manifold 36 at a tee fitting 42 and comprises a check valve 44, a first metering valve 46, a supercritical fluid extraction column 48, and a second metering valve 50. The pressure in the sample extraction column 48 is monitored by a gauge 56, and its temperature is controlled by a heater indicated at 55 surrounding the extraction column 48. Metering valves 46 and 50 permit separate control of the rates of flow into and out of the column 48, and allow control of the pressure drop across the column 48 to any desired value. At least the second metering valve 50 is heated to avoid freeze-up when used as a pressure reducer; that is, when used to reduce the fluid pressure to a lower value for subsequent sample separation. The column 48 is preferably connected to the metering valves by quick disconnect fittings 52 and 54, allowing columns 48 containing matrices from which samples are to be extracted to be readily connected and removed.

Briefly, in supercritical fluid extraction of a sample from a matrix, a matrix to be analyzed for constituents of interest is placed in a supercritical fluid extraction column 48. The extraction module 40 may be operated in a static mode wherein the supercritical fluid, typically $CO_2$, plus modifier if desired, are admitted to the column 48 and allowed to equilibrate for a period of time, before flow through the column is established. Alternatively, the extraction module 40 can be operated in a flow-through mode in which the supercritical fluid flows through the matrix, dissolving and removing various constituents of the matrix and various contaminants for which the matrix is to be analyzed. For example, in analysis of a fish sample for the presence of pesticides, the matrix might comprise comminuted fish flesh, possibly mixed with a diatomaceous earth or the like to remove or adsorb moisture. The extracted sample would consist principally of lipids, i.e., fatty molecules and oils. The supercritical fluid dissolves the lipids and removes them from the matrix. Industrial contaminants, such as polychlorinated biphenyls (PCBs), polyaromatic hydrocarbons (PAHs), or pesticides, such as DDT, are extracted together with the lipids. Such contaminants may be subsequently separated from the lipids in the sample separation module 58 associated with the supercritical fluid extraction module 40. The analytes are thus enriched to a level such that a subsequent chromatographic method employed for separation and detection of the contaminant is not compromised by coextractives, such as lipids, in the sample extract. In the preferred embodiment, each of the supercritical fluid extraction modules 40 is associated with a sample separation module 58. In a particularly preferred embodiment of the invention, each of the sample separation modules 58 comprises up to three different types of sample collection and/or separation apparatus capable of individual selection by an operator using a multi-port valve 60. Thus, for example, one collection device is simply a sample collection vessel 62 containing a suitable liquid solvent. The sample eluting from the supercritical fluid extraction column 48 passes by way of a port A of the multi-port valve 60 and a check valve 64 into the flask 62. In this case, the pressure drop across the metering valve 50, between the sample extraction column 48 and the flask 62, is large, thereby reducing the density of the mobile phase to a level such that the solubility of the analytes and coextractives in the gaseous fluid is negligible. The analytes and coextractives are collected in the flask 62, and the gaseous fluid is simply vented by way of a check valve 66, a carbon filter 68 and a vent line 70. In order to improve sample recovery efficiency, flask 62 is desirably kept cool by means of a thermoelectric heat pump 63. The sample remains dissolved in the solvent and can subsequently be analyzed as desired; for example, the sample can either be analyzed by gas chromatography or mass spectrometry as well known in the art, or further concentrated by evaporation of the solvent prior to analysis, as disclosed in U.S. Pat. No. 4,604,363. Such further processing and analysis of the sample is indicated generally at 65 and may also include adsorption or size exclusion separation performed employing the system of the invention. This possibility can be implemented by supply of the collected solvent via line 61, controlled by valve 67, and tee fitting 69 to the inlet port of valve 60.

A second sample separation and/or clean-up possibility which may be provided according to the invention in one or more of the sample separation modules 58 is selective adsorption of individual constituents of the sample on an adsorbent media and subsequent desorption with an appropriate liquid or supercritical fluid solvent. An adsorption column 72 is connected to a port B of the multi-port valve 60 to implement this possibility. Adsorption column 72 can contain any of a wide number of adsorptive materials. For example, in clean-up of pesticides in lipids, the sample can be trapped on adsorbents such as silica (preferably that sold by Floridin Company of Berkeley Springs, W. Va., as "Florisil") or alumina. Florisil in particular is useful for clean-up of small samples of fat containing low polarity pesticides. The sample eluting from the adsorption column 72 passes by way of a check valve 74 into solvent reservoir 62. As described above, if the supercritical fluid is used as the mobile phase for removing the constituents of the sample from the adsorption column, it may be vented from solvent reservoir 62.

According to an important aspect of the invention, apparatus for size exclusion chromatography (SEC), sometimes also termed gel permeation chromatography (GPC), is provided in one or more of the sample separation modules 58. More particularly, it has been found that a particular size exclusion chromatographic media, namely, polystyrene divinyl benzene beads of approximately 5–10 micron diameter, having porous surfaces, and most particularly porous surfaces having mean pore diameters on the order of 50 Å or less, are particularly suitable for separating samples prepared using supercritical fluid extraction. This medium is manufactured by the Phenomenex Corp. of Torrance, Calif. Columns of this medium suitable for SEC/GPC are marketed under the trademark ENVIROSEP-ABC by ABC Laboratories, Columbia, Mo. In particular, these media can be repeatedly exposed to $CO_2$ at supercritical pressures and temperatures without substantial degradation. This is not possible with commonly used prior art gel permeation resins such as that known as S-X3.

Accordingly, such polystyrene divinyl benzene beads are provided in a principal size exclusion chromatographic column 76 connected to port C of valve 60. Preferably a separate guard column 78, physically somewhat shorter but containing the same material, is provided upstream of the chromatographic column 76, and a valve 80 is provided to allow bypass of the downstream column 76. Columns 78 and 76 may be heated, as indicated.

Guard column 78 has several possible uses. For example, if it is anticipated that the extracted sample contains a relatively large amount of an unwanted constituent, such as lipids, the guard column 78 can be used to trap the SFE extract while allowing the extracting fluid to pass into the sample collection vessel. Selective elution of the lipids or other high molecular weight coextractive(s) through the guard column 78 is performed using either the supercritical fluid mixture available in the receiver 28 (possibly at lower pressure) or any other suitable fluid as the mobile phase. Elution of the analytes of interest, e.g. pesticides, is delayed due to their smaller molecular size. A detector 81 may be employed to obtain the elution profile of the sample constituents from the guard column 78, and thereby determine the time at which the elution of lipids (or other coextractives) is terminated. In the case of pesticides in a lipid-rich sample, the detector 81 may be an ultraviolet detector and sensor combination operating at 254 nm. When the beginning of a pesticide elution peak is observed, indicating that most of the larger lipid molecules have eluted, valve 80 can be actuated to its alternate position, so that the larger principal size exclusion chromatographic column 76 is presented with a relatively lipid-depleted, contaminant-rich sample from the guard column 78.

In applications requiring fractionation of pesticides from fat, the principal SEC column 76 is suitable, for example, for fractioning a 0.5 gram sample into successive eluents, the first containing at least 85% of the original lipid material and the second containing 85% of the original pesticides. This two-step process allows relatively small amounts of the contaminant of interest to be effectively separated from large quantities of lipids or other coextracted constituents of the sample, thereby greatly facilitating subsequent chromatographic analysis of the SFE extract.

An adjustable flow restrictor 82 may be provided in the line connected to the exit port of the column 76 to control the pressure drop across the column 76. The sample eluting the column 76 is directed to the sample collection vessel 62. If the supercritical fluid (deliverable through line 110) is used as the mobile phase for the separation carried out in the column 76, its pressure is reduced to a level close to atmospheric by adjustable flow restrictor 82 so that it may be vented from vessel 62 as described above. A check valve 84 is provided to eliminate any back flow into adjustable flow restrictor 82.

In some cases it may not be desirable to employ the supercritical fluid as the mobile phase in adsorption separation carried out employing adsorption column 72, or in size exclusion chromatography carried out employing one or both of polystyrene divinyl benzene packed columns 76 and 78. Accordingly, one or more reservoirs 86, 88 of suitable solvents, such as methylene chloride, tetrahydrofuran, hexane and toluene or mixtures thereof, are provided together with suitable respective valves 90, 92, a pump 94, and a shutoff valve 96 connected to a cross fitting 98 disposed downstream of metering valve 50. For example, after adsorption column 72 has trapped the extracted sample from the corresponding supercritical fluid extraction column 48, the solvent from one of reservoirs 86, 88 can be pumped by pump 94 to serve as the mobile phase, forcing the pesticides (or other analytes) through column 72 via multiport valve 60, and selectively separating the analytes from the adsorbed sample extract. Suitable piping (not shown) is provided to allow the solvents in reservoirs 86, 88 to be similarly supplied to other sample separation modules 58.

In order to calibrate the system, a sample loop 100 of known volume, e.g. 5 ml, may be connected to a two position, four port valve 102, in turn connected to a port D of the multiple port valve 60. Sample loop 100 can be filled with a known amount of solvent and/or sample and then supplied via a tee fitting 104 to the size exclusion chromatography column 76 to calibrate the column response to known sample and solvent materials. Valve 102 also provides a bypass path around guard column 78 both for rinsing column 76 and to provide additional flexibility in choice of the separation process.

The vent of each collection vessel 62 can be connected to an electronic mass flowmeter 105. The density of the supercritical fluid mobile phase will normally be known so that the value for the amount of gas vented, as measured by flowmeter 105, can easily be converted to determine the mobile phase flow rate. The output signal from the mass flowmeter 105 can be converted from analog to digital form in a suitable converter 106 to provide cumulative gas flow data as indicated at 108.

The sample extraction modules 40 and sample separation modules 58 thus extract the sample from the matrix in which it is found and separate it into its constituent parts, respectively. The constituents may subsequently be quantified and identified by any of a number of known processes, such as gas chromatography, mass spectrometry, or ultraviolet absorption measurements carried out employing detector 81. Detector 81 may comprise a source 83 of ultraviolet radiation, e.g. at 254 nm when used for lipid detection, and an appropriate sensor 85, on opposite sides of a transparent sample tube 87. Solvent exchange and/or sample concentration by evaporative analysis, as disclosed in U.S. Pat. No. 4,604,363, can also be accomplished on-line with the separation step. Such "downstream" processes, indicated generally at 65, can be carried out by either on-line pumping of the sample solution from reservoir 62 as it elutes from the corresponding separation unit or subsequent to further sample clean-up.

Any one of the fluids in tanks 10, 12 or 14 or a mixture thereof can be employed as a rinse solvent via valve 116 and line 114 to flush the extraction column 48 and associated elements, or to rinse out any possible contaminants accumulated downstream of the extraction column 48 from the separation module 58. Line 110 and valve 112 provide a flow path whereby the mixture of supercritical fluid and modifier solvent in receiver 28 can similarly be employed to rinse, for example, sample separation columns 76 and 78. Alternatively, solvents from vessels 86, 88 can be supplied by pump 94 through valve 96 and cross fitting 98 to rinse the sample separation columns 78 and 76, with valve 112 in its closed position.

Figure 2:
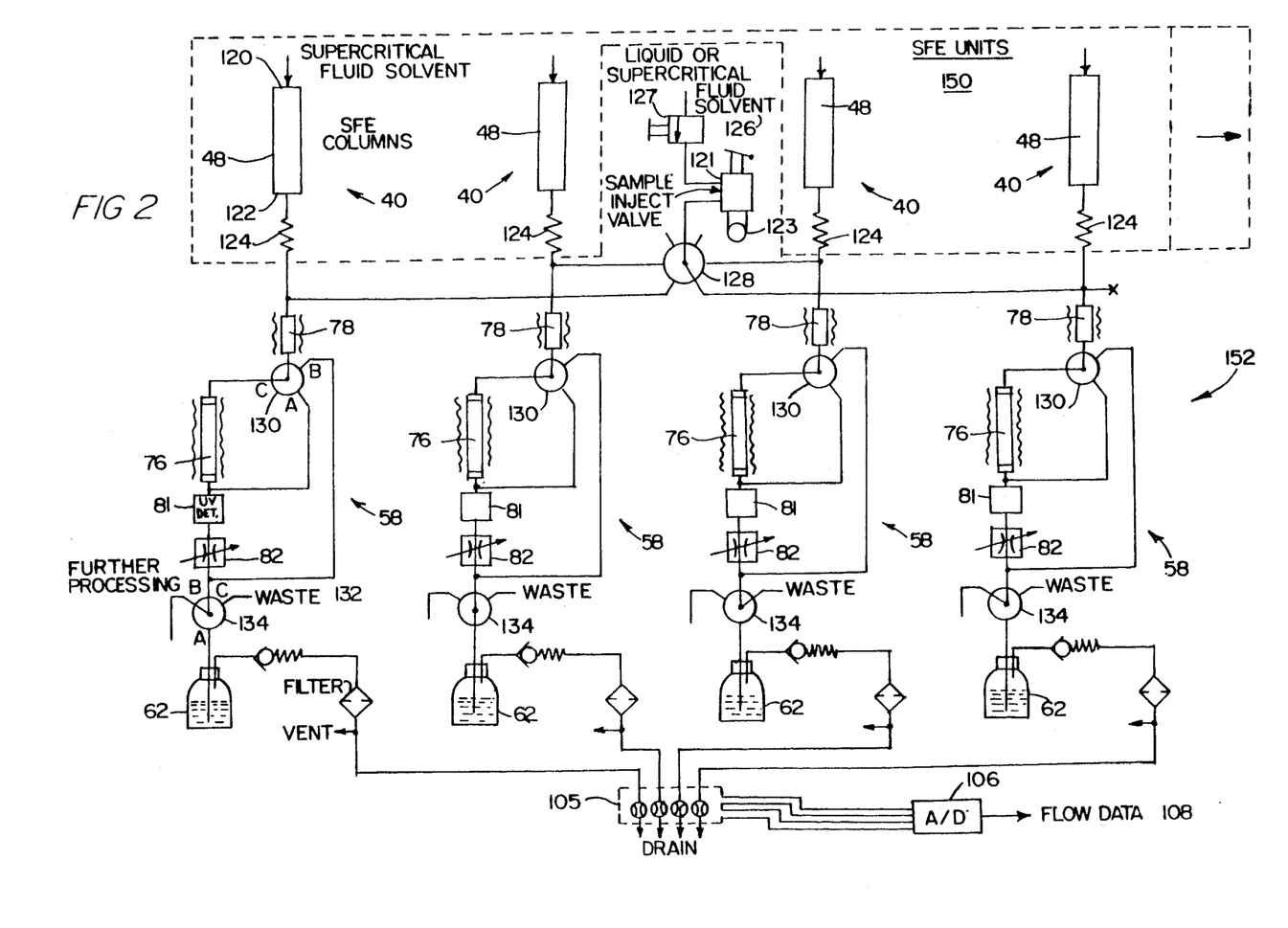
FIG. 2 is a schematic flow diagram of a portion of a particular embodiment of the invention, comprising four identical supercritical fluid extraction and sample separation modules.

FIG. 2 shows one implementation of an instrument of the invention comprising an extraction section 150 having four sample extraction modules 40, and a separation section 152 having four size exclusion separation modules 58. The adsorptive separation equipment shown in FIG. 1 is eliminated in this embodiment. While each sample extraction column 48 is followed by series-connected size exclusion chromatography columns 78 and 76, the separation modules are also capable of processing SFE samples from any existing SFE unit. A single instrument may incorporate as many as twenty sample extraction modules 40 and twenty sample separation modules 58. A sample extracted in another SFE unit to be concentrated and separated using one of the sample separation modules 58 can be injected by way of a four-port sample injection valve 121. A sample loop 123 is connected to sample injection valve 121 to allow a calibrated sample to be supplied to the size exclusion columns, as discussed above. If the sample is an extract eluting from one of the integrated SFE columns 48, it is typically trapped at the head of the corresponding guard column 78 after expansion through capillary restrictor 124 or an expansion valve. The guard column 78, as described above, is preferably packed with high porosity polystyrene divinyl benzene resin beads. As indicated above, it currently appears that the optimum mean pore diameter of these beads for certain commonly performed separations is 50 Å or less. The mobile phase for size exclusion chromatography can be either the supercritical fluid or one or more conventional solvents, admitted via valve 127 as indicated at 126. The mobile phase is preferably a $CO_2$ based supercritical fluid in order to reduce or eliminate the use of toxic organic solvents such as dichloromethane. The mobile phase may be directed to any of the sample separation modules 58 by a multiport valve 128. The guard column 78 and size exclusion column 76 can be heated to avoid freeze-up and solidification of the SFE extract due to expansion of the supercritical fluid therein.

As suggested above, size exclusion chromatography is preferably performed according to the invention employing plural series-connected columns containing the same media. A first guard column 78 is typically employed for trapping sample extracts and preliminary sample clean-up, that is, partitioning of the bulk constituents of the sample from the analytes, or only as a trap for sample extracts. The larger, more expensive column 76 is thus protected from possible clogging by non-elutable substances. In many cases the bulk of the sample comprises large molecules such as lipids or the like, while the constituents of interest, which elute somewhat later, are smaller molecules such as pesticides, PCBs, PAHs, or the like. In cases where the sample extract contains more than 0.5 gram of lipids it may be desirable to pass the separated sample fluid initially eluting from the column 78 directly to a UV detector 81 via a multiport valve 130 to determine when the pesticide or other analyte of interest begins to elute. Alternatively, the early eluting fraction can simply be directed to waste, as indicated at 132, by means of a further port B of the valve 130 and a second multiport valve 134.

When a given fraction of the sample has eluted, or when an analyte of interest is detected by detector 81, or simply after passage of a given interval of time based on prior experience, multiport valve 130 can be used to select port C. The remaining sample in column 78 now passes through a second column 76, preferably packed with the same polymer material, for further size-exclusion separation of the later-eluting constituents.

The sample initially eluting from column 78, and subsequently from column 76, may be collected in a quantity of solvent in a cooled collection vial 62. The separated fluid eluting from the column 76 is dispersed into the solvent, leaving the sample dissolved in the solvent and venting the supercritical fluid. Restrictor 82 is used to reduce pressure to approximately atmospheric.

Alternatively, by adjusting the second multiport valve 134 to a position B, the sample eluting from the column 76 can be directed to further processing steps, such as evaporative analysis as described in U.S. Pat. No. 4,604,363 mentioned above. Further, as noted above, size exclusion chromatography in column 76 and/or 78 may be preceded by an initial step of solvation of the sample in reservoir 62 and venting the supercritical fluid employed for initial extraction of the sample from the matrix.

The structure of the system of the invention having thus been described, the following provides additional details concerning the structure of the individual components and the typical sequence of system operation. As discussed above, it is an object of the invention to provide an integrated instrument providing for initial supercritical fluid extraction of the sample from the matrix, combined with highly versatile sample separation processing. More preferably, each of a plurality of supercritical fluid extraction modules can be connected to a corresponding sample separation module, each providing a choice of several sample separation options. Still more particularly, the system is designed to provide supercritical fluid extraction of the sample from the matrix followed by size exclusion chromatographic separation of the sample into its constituent parts.

It will be recognized as well that the supercritical fluid extraction section 150 of the invention is useful for sample extraction for subsequent sample clean up and extraction instruments other than those described in detail. Similarly, samples extracted using extraction techniques not according to the inventive system as described may be cleaned up and/or fractionated and/or analyzed using the separation section 152 of the instrument according to the invention.

To accomplish these objects the following system specifications are preferred:

The system accommodates matrices of 0–100 grams.

Matrices are presented to the system by placing them in individual supercritical fluid extraction columns. The matrices are prepared by comminution, or like conventional preparation steps, or may be premixed with a support material such as the diatomaceous earth sold as "Chem Tube-Hydromatrix" by Analytichem International, for reducing moisture in the sample. This option is discussed in Hopper et al U.S. patent application Ser. No. 07/536,861, filed Jun. 12, 1990.

The extraction columns are pressure rated at between 10,000 and 20,000 psig, depending on the particular process parameters chosen.

Differently sized supercritical fluid extraction columns may be provided to accommodate wide ranges of sample sizes. To facilitate operation, the supercritical fluid extraction columns are fitted with quick disconnect fittings mating identically with the associated piping regardless of the sample column size provided.

Independent temperature controls are provided for each of the supercritical fluid extraction columns, providing temperatures between ambient and 300° C. A high capacity accumulator (typically 600 cc) is provided to allow storage of large volumes of supercritical fluid, including modifier solvent where desired, to deliver continuous non-pulsating flow to either the SFE columns or the SEC columns and to accelerate start-up of the supercritical fluid SEC process. The accumulator as well as the separation columns and metering valves are temperature controlled between ambient and 250° C.

For safety, pressure rupture disks and release valves provide defined exhaust paths for the over pressurized supercritical fluid. A solenoid-operated relief valve is provided to drain the accumulator when needed.

Both the supercritical fluid, typically $CO_2$, and the modifier are pumped by individual separately controllable pumps to provide substantially unlimited variation in the relative proportions of supercritical fluid and modifier in the mixture stored in the accumulator vessel.

More specifically, in a preferred embodiment the $CO_2$ pump 22 is a modified Haskel model DSHF-151 air-driven liquid pump capable of generating flow rates of up to 1.1 liters/min at pressures up to 20,000 psig. This relatively large flow capacity allows for simultaneous extraction of up to sixteen samples of up to 100 cc in a reasonable time. To suit this pump to the integrated instrument of the invention, an external pilot allowing the pump to be started and stopped remotely with a solenoid valve, a three way cycling spool allowing pumping of liquified gases under pressure, and a stroke counter that counts each pump cycle for control of pump output may be added. The modifier pump 24 may similarly be a modified Haskel Model 29723 air-driven liquid pump with a liquid displacement of 0.6 ml/min with pressures up to 12,000 psig. This pump is also equipped with an electronic stroke counter. Both pumps 22 and 24 are preferably supplied by Haskel in various eliminating automatic cycling, and such that a complete cycle is accomplished by a momentary pneumatic impulse at the signal port. The ratio of the supercritical fluid to modifier solvent can be controlled by control of the number of pneumatic impulses provided to the signal ports of the pumps 22 and 24. This control arrangement is particularly suitable for digital computer control of the overall system of the invention.

An adsorption trap 20 is provided between the $CO_2$ tank 10 and the $CO_2$ pump 22 (see FIG. 1). This trap preferably contains porous glassy carbon to remove contaminants such as PAHs and PCBs present in the carbon dioxide. Other traps, such as a carbon molecular sieve (Carboxen-56, Supelco, Inc., Bellefonte, Pa.) capable of retaining small organic molecules, alumina, or "Hydromatrix" diatomaceous earth may also be employed.

The heated receiver 28 may be Haskel model No. 15712-2 and is kept at a temperature such that the fluid mixture is always either gaseous or supercritical. An Ashcroft type K1 transducer may be used to sense receiver pressure. Preferably the transducer signal is digitized for convenient automation of pressure control. Any drop below the desired receiver pressure causes the pumps 22 and 24 to be activated to deliver the fluid mixture until the receiver pressure equals or exceeds the desired set point pressure.

Each of the heated elements is provided with a custom designed heater. These heaters are preferably made from silicone rubber or mica, available from Watlow Electric Corporation (St. Louis, Mo.). Thermocouples inserted between the heaters and the heated elements are used to sense the element temperatures and to provide a suitable temperature control signal.

The extract from the supercritical fluid extraction column is trapped in either a liquid solvent, or in an adsorbent porous matrix such as Alumina-C (Universal Scientific, Inc.), "Hydromatrix" diatomaceous earth, or in one of several columns packed with a size exclusion chromatographic media, preferably 5-10 micron polystyrene divinyl benzene beads having porous surfaces wherein the mean pore diameter is 50 Å or less. Temperature control of the liquid solvent and of the adsorption and size exclusion columns is provided to prevent freeze up and also to provide further process parameter flexibility.

Finally, all lines downstream of the pumps as well as the extraction and separation columns are accessible for rinsing with appropriate solvents. Piping is provided to allow rinsing of the supercritical extraction columns and the adsorption and size exclusion chromatography columns with the supercritical fluid or the modifier solvent, and to also allow rinsing of the separation columns with the solvents provided for use as the mobile phase in sample extraction and/or separation.

Operation of the instrument of the invention commences with activation of the heaters so as to heat all the heated elements to their desired operating temperatures. Pumps 22 and 24 are primed by bleeding out any air in their lines through downstream vent valve 23 (FIG. 1) and allowing the pumps to cycle for about fifteen seconds. Liquid $CO_2$ exiting from valve 23 indicates that the lines have been properly bled. A regulating relief valve 25 downstream of the $CO_2$ shut-off valve 18, that is, between the pump 22 and the tee fitting 26, serves to maintain enough backpressure at the outlet of pump 22 to ensure that a positive pressure gradient exists between the pump inlet and pump outlet. This gradient prevents free flow of $CO_2$ into the receiver 28. Free flow of $CO_2$ may cause rapid cooling and alter the modifier/$CO_2$ ratio. A mixture of $CO_2$ and modifier of set volumetric ratio (0-1) is then pumped into the receiver 28 at a controlled rate. The fluids mix at the tee 26 downstream of the relief valve and then flow into the receiver 28. Valve 34 and/or 50 is kept shut during this fill up period.

The supercritical fluid extraction section 150 may comprise up to twenty identical supercritical fluid extraction modules 40. Each module includes an extraction column 48, provided with a check valve 44 to isolate the extraction columns and avoid cross contamination between them, an inlet metering valve 46, and an outlet metering valve 50 (FIG. 1). Suitable components are available from Butech Pressure Systems.

The metering valves 46 and 50 are used to provide accurate control of fluid flow rates as well as flow shut off, and to create a pressure drop from the receiver pressure down to the desired operating column pressure. Flow restrictors 124 (FIG. 2) may alternatively be employed for the same purpose. A pressure gauge 56 is used to read the column pressure.

Each of the supercritical fluid extraction columns 48 comprises a cylindrical stainless steel tube and associated fitting collars, both available from Butech Pressure Systems. The samples are held in place in the column by means of stainless steel, ten micron porosity frits located at either end of the columns 48.

As discussed above, matrices from which samples are to be extracted are placed in these columns 48 in their original form, or prepared by comminution and drying, or are mixed with diatomaceous earth such as that sold under the trade name Hydromatrix. Use of the Hydromatrix material provides both sample support as well as adsorption of interfering sample moisture, as discussed in Hopper et al U.S. patent application Ser. No. 7/536,861.

Extraction may take place in either a static mode or in a continuous flow, on-line mode. In the static mode, the supercritical fluid solvent is admitted to the column 48 through valve 46 and permitted to equilibrate with the sample in the matrix at any desired pressure and for any desired period before resuming flow through valve 50. In the continuous flow mode, the supercritical fluid flowing through the column 48 experiences a desired pressure drop controlled by the relative apertures of valves 46 and 50. The choice of mode may be dictated by either the sample and matrix characteristics or the need for either qualitative or quantitative extraction. Solvent flow rate through metering valve 50 is monitored with electronic mass flow meter 105. An output signal from the electronic mass flow meter 105 is digitized in analog to digital converter 106 and used to evaluate cumulative gas flow, as indicated at 108.

At the end of a static extraction, the supercritical fluid mixture loaded with the sample is expanded through the second metering valve 50. Expansion at this metering valve 50 normally causes a substantial drop in fluid temperature. Accordingly the metering valve 50 is heated to prevent freeze-up and to ensure that the fluid mixture is kept at adequate temperature throughout the expansion stage.

After supercritical fluid extraction as described above, the sample is supplied via cross fitting 98 to multi-port valve 60 wherein it is directed to one of several different sample extraction devices or to several devices in sequence. As indicated above, each of the supercritical fluid extraction columns 48 is associated with at least one of several different sample extraction devices; in an ultimate realization of the system having maximum versatility, each of the sample extraction columns 48 is associated with each of three different types of sample extraction device.

Alternatively, the supercritical fluid extraction columns 48 might all be connected to a manifold via suitable shut-off valves, while the sample extraction devices might similarly be connected to the manifold using shut-off valves. This would provide versatility in the choice of sample separation device without requiring duplication of equipment. However, this expedient would involve loss of relatively substantial amounts of sample in the manifold, would not allow simultaneous on-line SFE/SEC of more than one sample, and might thus be satisfactory only in systems intended to be used for analysis of relatively large quantities of sample.

Four principal methods of sample separation are provided in the embodiment of the sample separation module 58 shown in FIG. 1. Such a sample separation module 58 may be connected to each of the sample extraction modules 40. These four methods include (1) trapping the extract in an appropriate solvent in a solvent reservoir 62 and subsequent concentration, for example, using evaporative analysis as disclosed in U.S. Pat. No. 4,604,363; (2) selectively trapping constituents of the extract in an adsorption column 72, rinsing the sample from the column with an appropriate solvent, and then clean-up and concentration, for example, again using evaporative analysis; (3) trapping the extract in a guard column 78, eluting co-extractives with a supercritical fluid or an appropriate conventional solvent and cleaning up the extract using size exclusion column 76; and (4) trapping the extract at the head of the size exclusion column 76 and performing on-line extract clean-up with a supercritical fluid and/or appropriate conventional solvent. As a further option, method (1), trapping the extract in the solvent in reservoir 62, may be followed by any of methods (2)–(4). The flow path provided for this option includes line 61, valve 67 and tee fitting 69.

Referring to option (1), possible solvents might include hexane, methanol, dichloromethane, toluene or benzene. The extracted solution can be directly analyzed, or may be further cleaned-up, for example, in SEC column 76 and concentrated using the evaporative system disclosed in U.S. Pat. No. 4,604,363 referred to above, all as indicated at 65.

In option (2), the extract from the matrix eluting as part of the sample can be retained in one of a variety of solid-phase extraction traps contained in adsorption column 72. The sample fluid eluted from the adsorption columns 72 can then be analyzed using conventional or supercritical fluid SEC and evaporative analysis, or otherwise. As indicated, the mobile phase for eluting the adsorbed material from the adsorbent may be the supercritical fluid or can be one of several solvents stored in reservoirs 86 and 88. Adsorbent materials of principal interest include alumina, Florisil or other silicas, any of cyanopropyl, diol, porous glassy carbon, or hypersil-ODS, all available from Keystone Scientific, Bellefonte, Pa., Tenax-TA available from Enka Research Institute of Holland, polyurethane foam, diatomaceous earth and zeolites. As will be appreciated by those of skill in the art, these materials are weak adsorbents for chemicals but are much more adsorbent of water. The choice of the adsorbent material depends on the nature of the analyte as well as the ability of an appropriate liquid or supercritical fluid solvent to rinse out the adsorbed analytes. None of the above materials lends itself, however, to size exclusion chromatography using supercritical fluid as the mobile phase. This process is highly desirable, for reasons mentioned above. Therefore, according to one aspect of the invention, each separation module 58 includes one or more SEC columns 76 and 78 packed with beads of polystyrene divinyl benzene, as this material can separate even highly polar substances, and is suitable for use with supercritical $CO_2$ as the mobile phase.

According to a particularly useful aspect of the present invention, supercritical fluid sample extraction (SFE) is combined in options (3) and (4) for the first time in an integrated system with size exclusion chromatography (SEC), preferably using beads of polystyrene divinyl benzene material approximately 5-10 microns in diameter, having pores of mean diameter 50 Å or less. It has been found that this material, produced by Phenomenex Corp. of Torrance, Calif., and marketed in columns by ABC Laboratories as ENVIROSEP-ABC is capable of withstanding repeated pressure cycles from atmospheric pressure to 10,000 psig with no manifest structural damage or morphological ablation, such that supercritical $CO_2$ or other supercritical fluid can be used as the mobile phase for size exclusion chromatography. This material can accordingly be used for fractionation, for example, of numerous pesticides from corn oil and fats and for separating a variety of low molecular weight fruit, vegetable and soil extracts from their original matrices. These analyses are highly useful in responding to current environmental concerns.

In a particularly preferred arrangement, the same material is used as the packing in a first SEC guard column 78 and in a larger principal SEC column 76. A valve 80 is provided to allow bypass of the principal column 76, trapping the SFE extract in guard column 78, so that the early-eluting constituents do not clog the pores of the packing of the principal separation column 76. The pressure at which the SFE extract is trapped can be either low supercritical or subcritical. Preliminary partitioning of the sample extract in the SEC guard column 78 reduces the amount of sample to be processed in the principal SEC column 76 within its capacity level (0–1 g) to separate lipids in a sample. Alternatively, a flow path is established from port D of multiport valve 60 through sample injection valve 102, to allow bypassing the guard column 78 where desired. In this way a particular sample can be separated in either the guard column 78, the main column 76 or both in sequence.

The output flows from the columns 76 and 78 are piped to UV detector 81, and the flow rate through the assembly is controlled by adjustable flow restrictor 82.

As explained above, the mobile phase used to fractionate the sample in columns 78 and 76 can be the supercritical fluid itself, with or without modifier, or can comprise one of a number of solvents contained in reservoirs 86 and 88. Typical solvents may include methanol, hexane, toluene, Freon-22, dichloromethane, tetrahydrofuran or a mixture thereof.

A typical process employing both the guard column 78 and the main column 76 is as follows. With valve 80 initially in the position shown in FIG. 1, such that main column 76 is bypassed, the high molecular weight early eluting co-extractives are separated from the sample in guard column 78 using a liquid solvent such as dichloromethane or a supercritical fluid solvent such as $CO_2$, with or without modifier. A fraction of the high molecular weight constituents of the sample thus having been removed, valve 80 is actuated to its alternate position so that the low molecular weight constituents are then separated in principal SEC column 76. The mobile phase for this portion of the separation may again be a solvent such as dichloromethane or may be a supercritical fluid solvent such as $CO_2$, with or without modifier. After separation in column 76 and pressure reduction in restrictor 82, the sample may be recovered in a solvent reservoir 62 and can be analyzed by evaporative processing, or the like, for co-extractives and analytes.

In applications where the extract is expected not to contain any non-eluting material, and the mass of extract is less than about 0.5 grams, the separated sample can be diverted around the guard column 78 by the flow path including port D of valve 60 and sample inject valve 102, thus being injected directly into the head of the main column 76, and subsequently separated with an appropriate mobile phase, either the supercritical fluid or a conventional solvent.

Calibration of the system is provided by a sample loop 100 connected to sample injection valve 102. A sample of known constituents can be injected into the sample loop for exact control of its volume and then separated in the main column 76 using a known solvent.

Given the specific constructional and functional details provided above, those of skill in the art will have no difficulty in practice of the invention. Preferably the entire system is controlled by a programmable computer, capable of actuating the valves, operating the pumps, and controlling the temperature and pressure at various points in the system as described above. In this regard, reference may be made to copending application Ser. No. 07/347,519, incorporated herein by reference, which discloses a computer-controlled single-loop chromatography system. Similarly, the choice of components not specifically mentioned above is within the skill of the art. In the computer-controlled embodiment of the invention, it is convenient to employ pneumatically operated valves, with the computer operating solenoids controlling the supply of compressed air to the operating cylinders of the valves. As noted above, the modified pumps 22 and 24 employed in the preferred embodiment of the invention are particularly suitable for computer control of the ratio of the supercritical fluid to modifier solvent.

It will thus be appreciated by those of skill in the art that the system described meets the needs of the art and the objects of the invention discussed above. An integrated instrument enabling supercritical fluid extraction of a number of samples coupled with individual sample separation devices, each including a number of options, is provided. Each of the sample extraction and separation columns is provided with separate pressure and temperature controls to enable wide variation of process parameters. Analysis of the sample after separation can be carried out using any of a number of known techniques. The supercritical fluid or one of several solvents can be used as the mobile phase for sample separation. Similarly, either the supercritical fluid or the solvents can be used for subsequent flushing of the columns to prepare them for the next sample.

While several preferred embodiments of the invention have been discussed in detail, those of skill in the art will recognize that numerous modifications and improvements can be made thereto without departing from the spirit and scope of the invention. Accordingly, the invention is not to be limited by the above exemplary disclosure but only by the following claims.

What is claimed is:

1. An apparatus for supercritical fluid extraction of a sample from a bulk matrix, followed by supercritical fluid separation of the extracted sample into its constituents, comprising a number of separate supercritical fluid extraction modules with independent temperature, pressure, and flow rate control, said apparatus further comprising:
   supply means for supply of a supercritical fluid,
   a plurality of supercritical fluid sample extraction columns, each having an inlet and an outlet, and being constructed to contain said supercritical fluid,
   means for individually establishing fluid flow communication between the inlets of individual ones of said extraction columns and said supply means in order to extract a sample from a matrix disposed in the sample extraction column; and
   a like plurality of sample separation means, each having an inlet in fluid flow communication with the outlet of a corresponding respective sample extraction column, for separating the extracted sample into its constituents.

2. The apparatus of claim 1, wherein said supply means comprises a source of a gas under pressure and a source of a modifier compound, means for mixing the gas with the modifier compound to constitute a supercritical fluid, and means for controlling the relative proportions of the gas and the modifier compound in the supercritical fluid.

3. The apparatus of claim 2, wherein said means for controlling the relative proportions of the gas and modifier compound comprises first and second pumps in fluid flow communication with said sources of gas and modifier compound, respectively.

4. The apparatus of claim 3, wherein the pumping rates of said first and second pumps are separately controllable to control the relative proportions of said gas and modifier compound in said supercritical fluid.

5. The apparatus of claim 3, further comprising a heated pressure vessel for storing the mixture of gas and modifier compound under supercritical conditions.

6. The apparatus of claim 1, wherein each supercritical fluid sample extraction column is provided with means for control of its temperature.

7. The apparatus of claim 1, wherein each sample extraction column is provided with means for control of the pressure therein, independent of the pressure of said supercritical fluid as supplied from said supply means.

8. The apparatus of claim 7, wherein each supercritical fluid sample extraction column may be operated in a static or an on-line mode, said apparatus further comprising means for control of the pressure drop across each of said supercritical fluid sample extraction columns when operated in an on-line mode.

9. The apparatus of claim 8, wherein said means for control of the pressure drop across each supercritical fluid sample extraction column comprises first and second metering valves in fluid flow communication with the inlet and the outlet of each said sample extraction column, respectively.

10. The apparatus of claim 9, wherein one or both of said metering valves are heated.

11. The apparatus of claim 1, wherein each of said sample separation means comprises at least one of:
   (a) collection vessel means for containing a quantity of solvent liquid, for collecting the sample eluted from the corresponding supercritical fluid sample extraction column in said quantity of solvent liquid;
   (b) adsorbent means for adsorbing a constituent of interest from the sample eluted from the corresponding supercritical fluid sample extraction column, and means for subsequently removing the constituent of interest from the adsorbent means; and
   (c) size exclusion chromatography means for separating a constituent of interest from the sample eluted from the corresponding supercritical fluid sample extraction column.

12. The apparatus of claim 11, wherein said collection vessel means comprises means for reducing the pressure of the eluted sample to near-atmospheric, and means for allowing the sample to flow into said quantity of solvent liquid at a point located below the level of the liquid in the collection vessel, whereby the gaseous material of the supercritical fluid is vented.

13. The apparatus of claim 11, wherein said adsorbent means comprises an adsorption column packed with a solid phase extraction trap material.

14. The apparatus of claim 13, wherein said extraction trap material is selected from the group consisting of silica gel, alumina, silicic acid, diatomaceous earth, and zeolites.

15. The apparatus of claim 11, further comprising means for controllably reducing the pressure of the fluid eluted from the corresponding supercritical fluid sample extraction column in fluid communication between the outlet of each supercritical fluid sample extraction column and the inlet of the corresponding sample separation means.

16. The apparatus of claim 11, wherein said size exclusion chromatography means comprises one or more columns packed with a polymeric resin material capable of separating constituents of interest from unwanted constituents of said sample.

17. The apparatus of claim 16, wherein said size exclusion chromatography means comprises first and second series-connected columns packed with said polymeric resin material.

18. The apparatus of claim 16, wherein said polymeric resin material is substantially unaffected by repeated exposure to said supercritical fluid.

19. The apparatus of claim 16, wherein said polymeric resin material comprises beads of polystyrene divinyl benzene of approximately 5–10 microns diameter, having porous surfaces having pores of approximately 50 Å or less mean pore diameter.

20. The apparatus of claim 11, further comprising means for analysis of the eluent from said sample separation means in fluid flow communication therewith.

21. The apparatus of claim 20, wherein said means for analysis comprises a source of ultraviolet radiation for irradiating the eluent from the sample separation means, and a sensor means for monitoring the absorption of ultraviolet radiation from said source by the eluent.

22. The apparatus of claim 11, further comprising means for controlling the flow rate of the sample eluted from each of said supercritical fluid sample extraction columns through the corresponding sample separation means.

23. The apparatus of claim 11, further comprising means for permitting selection of a mobile phase for sample separation in the sample separation means.

24. The apparatus of claim 23, wherein said means for permitting selection of a mobile phase comprises means for controllable supply to said sample separation means of one of:
   said supercritical fluid;
   said supercritical fluid having been reduced in temperature and/or pressure; or
   one of one or more solvents.

25. An instrument for sample analysis, comprising supercritical fluid extraction apparatus for extraction of analytical samples from sample matrices, said apparatus further comprising:
   a source of supercritical fluid;
   a source of modifier solvent;
   means for proportional mixing of said supercritical fluid with said modifier solvent; and
   a plurality of supercritical fluid extraction columns, each comprising a pressure vessel having an inlet in fluid communication with said means for proportional mixing, and an outlet;
   a like plurality of means for separation of a sample extracted from a sample matrix in one of said extraction columns into its constituents, each said means for separation being in fluid communication with a corresponding outlet of one of said pressure vessels; and
   means for separately controlling the pressure and temperature in and flow rate of fluid through each of said columns.

26. The apparatus of claim 25, wherein said means for separately controlling the pressure in each of said columns comprises first and second controllable pressure reducing metering valves in flow communication with the inlet and outlet of each of said columns, respectively.

27. The apparatus of claim 26, wherein at least the second metering valve in flow communication with the outlet of each of said columns is heated.

28. The apparatus of claim 25, wherein said means for proportional mixing of said modifier solvent with said supercritical fluid comprises first and second individually controllable pumps in fluid flow communication with said sources of supercritical fluid and modifier solvent, respectively, and reservoir means for storing the mixture thereof.

29. An apparatus for supercritical fluid extraction of a sample from a matrix followed by supercritical fluid separation of the sample into its constituent parts, comprising a number of separate supercritical fluid extraction modules with independent temperature, pressure, and flow rate control, said apparatus comprising:
   a source of supercritical fluid, a plurality of supercritical fluid sample extraction columns, and a like plurality of corresponding sample separation units, at least some of said sample separation units comprising columns packed with adsorption media or size exclusion chromatographic media, each said supercritical fluid sample extraction column having a defined inlet port normally controllably connected in flow communication with said source of supercritical fluid, and a defined outlet port normally in fluid flow communication with a corresponding sample separation unit, and further comprising piping means for controllably establishing flow communication between the source of supercritical fluid and the outlet port of each said supercritical fluid sample extraction column, whereby the supercritical fluid sample extraction column may be rinsed with said supercritical fluid.

30. The apparatus of claim 29, further comprising means for rinsing each said sample separation column with said supercritical fluid.

31. A method of extracting a sample from a matrix, said sample containing a constituent of interest and one or more further constituents, and for subsequently separating said sample into its constituents, comprising the steps of:
   providing an instrument comprising means coacting to provide supercritical fluid extraction followed by supercritical fluid sample separation, including a number of separate supercritical fluid extraction modules with independent temperature, pressure, and flow rate control;
   placing the matrix in a supercritical fluid sample extraction column of said instrument;
   admitting supercritical fluid to the supercritical fluid sample extraction column and allowing the supercritical fluid to elute from the supercritical fluid sample extraction column together with the sample, while controlling the temperature and pressure within, and the flow rate through, said extraction column, admitting the eluting supercritical fluid together with the sample to a size exclusion chromatography column of said instrument, said chromatography column being packed with polystyrene divinyl benzene; and allowing the supercritical fluid to elute from said size exclusion chromatography column, such that the constituents of the sample elute from said size exclusion chromatography column together with the supercritical fluid, ordered by their relative molecular sizes.

32. The method of claim 31, wherein said polystyrene divinyl benzene is provided in the form of beads approximately 5-10 microns in diameter.

33. The method of claim 32, comprising the further step of analyzing and identifying the constituents of the sample eluting from the size exclusion chromatography column.

34. The method of claim 32, wherein said method is performed employing an integrated sample analysis instrument comprising a number of substantially identical supercritical fluid sample extraction columns, each connected to a corresponding sample separation module, at least one of said sample separation modules comprising at least one size exclusion chromatography column packed with polystyrene divinyl benzene, and at least one of said sample separation modules comprising a size exclusion chromatography column further comprising an adsorption column packed with a material which selectively adsorbs one or more of the constituents of the sample, and comprising the further step of selecting either the adsorption or size exclusion chromatography column to separate the sample eluting from the corresponding supercritical fluid sample extraction column.

35. The method of claim 34, comprising the further step of introducing the sample eluted from the corresponding supercritical fluid sample extraction column into a quantity of solvent contained in a collection vessel, such that the supercritical fluid is vented, leaving the sample dissolved in the solvent.

36. The method of claim 32, wherein the pores on the surfaces of said beads have an approximate mean pore diameter of 50 Å or less.

37. The method of claim 31, further comprising the step of separately controlling the pressure and temperature within each of said supercritical fluid sample extraction columns.

38. The method of claim 31, comprising the further step of selecting whether the supercritical fluid is maintained static within the matrix in the supercritical fluid sample extraction column for a period of time or is permitted to flow through the matrix.

39. The method of claim 38, comprising the further step of controlling the pressure drop across each supercritical fluid sample extraction column when operated such that said supercritical fluid is permitted to flow through the matrix.

40. An instrument for supercritical fluid extraction of a sample from a matrix and supercritical fluid separation of said sample into its constituents, comprising a number of separate supercritical fluid extraction modules with independent temperature, pressure, and flow rate control, and a number of sample separation modules, each of said separation modules being adapted to be placed into fluid flow communication with one of said supercritical fluid extraction modules to receive a sample eluted therefrom, and for separating said sample into its constituents, and said separation modules each further comprising:

(1) a source of supercritical fluid;
(2) a source of solvent;
(3) sample separation means; and
(4) controllable valve means for selectible supply of said supercritical fluid or said solvent to said sample separation means;

said sample separation means comprising at least one of:
(a) collection vessel means for collecting a sample eluted from the supercritical fluid sample extraction column in a quantity of solvent liquid;
(b) absorbent means for absorbing a constituent of interest from a sample eluted from the supercritical fluid sample extraction column, and means for subsequently removing the constituent of interest from said absorbent means; and
(c) size exclusion chromatography means for separating a constituent of interest from a sample eluted from the supercritical fluid sample extraction column.

41. The apparatus of claim 40, wherein said collection vessel means comprises means for reducing the pressure of the sample to near-atmospheric, and means for allowing the sample to flow into a quantity of solvent liquid below the level of the liquid, whereby the gaseous material of the supercritical fluid is vented and the sample comprising the constituent of interest remains dissolved in the solvent liquid.

42. The apparatus of claim 41, wherein said adsorbent means comprises an adsorption column packed with a solid phase extraction trap material.

43. The apparatus of claim 42, wherein said extraction trap material is selected from the group consisting of silica gel, alumina, silicic acid, diatomaceous earth, and zeolites.

44. The apparatus of claim 40, wherein said size exclusion chromatography means comprises one or more columns packed with a polymeric resin material capable of separating constituents of interest from unwanted constituents of said sample.

45. The apparatus of claim 44, wherein said size exclusion chromatography means comprises first and second columns packed with said polymeric resin material.

46. The apparatus of claim 44, wherein said polymeric resin material is substantially unaffected by repeated exposure to said supercritical fluid.

47. The apparatus of claim 44, wherein said polymeric resin material comprises beads of polystyrene divinyl benzene of approximately 5-10 microns diameter, having porous surfaces having pores of approximately 50 Å or less mean pore diameter.

48. The apparatus of claim 44, further comprising valve means for selectively controlling said sample to flow alternatively through said first column and bypass said second column, or through said first and second columns in series.

49. The apparatus of claim 40, further comprising means in fluid communication with said sample separation means for analysis of a separated sample eluting therefrom.

50. The apparatus of claim 49, wherein said means for analysis comprises a source of ultraviolet radiation arranged to irradiate the separated sample eluting from the sample separation means, and a sensor for monitoring the absorption of ultraviolet radiation by the eluting sample.

* * * * *